(12) United States Patent
Yamada

(10) Patent No.: US 7,871,373 B2
(45) Date of Patent: Jan. 18, 2011

(54) ENDOSCOPE DEVICE

(75) Inventor: Yuichi Yamada, Tokyo (JP)

(73) Assignee: Olympus Corporation, Tokyo (JP)

( * ) Notice: Subject to any disclaimer, the term of this patent is extended or adjusted under 35 U.S.C. 154(b) by 1105 days.

(21) Appl. No.: 11/568,906

(22) PCT Filed: May 12, 2005

(86) PCT No.: PCT/JP2005/008710

§ 371 (c)(1),
(2), (4) Date: Nov. 9, 2006

(87) PCT Pub. No.: WO2005/110188

PCT Pub. Date: Nov. 24, 2005

(65) Prior Publication Data

US 2007/0213592 A1 Sep. 13, 2007

(30) Foreign Application Priority Data

May 13, 2004 (JP) .............................. 2004-143612

(51) Int. Cl.
A61B 1/06 (2006.01)
(52) U.S. Cl. ....................... 600/175; 600/177
(58) Field of Classification Search .................. None
See application file for complete search history.

(56) References Cited

U.S. PATENT DOCUMENTS 4,415,240 A * 11/1983 Nishioka et al. .............. 385/33
4,706,653 A * 11/1987 Yamamoto .................. 600/175
4,747,661 A * 5/1988 Ohkuwa ..................... 385/118
4,787,370 A * 11/1988 Kanamori ................... 600/175
4,856,495 A * 8/1989 Tohjoh et al. ............... 600/175
4,860,732 A * 8/1989 Hasegawa et al. ........... 600/109
4,919,114 A * 4/1990 Miyazaki .................... 600/110
4,941,457 A * 7/1990 Hasegawa ................... 600/142
5,547,457 A * 8/1996 Tsuyuki et al. .............. 600/175
5,989,185 A * 11/1999 Miyazaki .................... 600/175
6,921,920 B2 * 7/2005 Kazakevich .................. 257/81

FOREIGN PATENT DOCUMENTS

| JP | 07-155286 | 6/1995 |
|---|---|---|
| JP | 10-216085 | 8/1998 |
| JP | 10-328129 | 12/1998 |
| JP | 11-244220 | 9/1999 |
| JP | 3194660 | 6/2001 |

* cited by examiner

Primary Examiner—Philip R Smith
(74) Attorney, Agent, or Firm—Dickstein Shapiro LLP

(57) ABSTRACT

This endoscope device is provided with: a laser light source that emits light having a specific wavelength; a diffusion optical component that diffuses light emitted from the laser light source and irradiates it onto an endoscopic examination subject at a distal end portion of an insertion portion; an adaptor that has a fluorescent substance that uses light from the laser light source as excitation light to emit light having a different wavelength, and is mounted on the distal end portion of the insertion portion such that it is able to be freely attached or removed; and a diffusion prevention component that is placed between the fluorescent substance of the adaptor and the diffusion optical component, and that prevents diffusion of light irradiated from the diffusion optical component.

13 Claims, 4 Drawing Sheets

ENDOSCOPE DEVICE

PRIORITY CLAIM

This application is a national stage 371 Application based on PCT Application No. PCT/JP2005/008710, filed on May 12, 2005, entitled "ENDOSCOPE DEVICE" whose priority is claimed on Japanese Patent Application No. 2004-143612, filed May 13, 2004. The contents of which are incorporated herein by reference.

BACKGROUND OF THE INVENTION

1. Field of the Invention

The present invention relates to an endoscope device that is used medically and industrially and the like, and, in particular, to an endoscope device that is provided with light for irradiating onto a test subject.

2. Description of Related Art

Conventionally, endoscope devices are widely used for observing interiors of living bodies and interiors of machinery and the like. In these endoscope devices illumination based on white light is typically used.

However, in recent years, as is described in Japanese Patent No. 3194660 and the like mentioned below, technology has been developed in which laser light of a specific wavelength is irradiated onto a subject of an endoscopic examination, and, using this laser light as excitation light, fluorescence emitted by the endoscopic examination subject is observed. Alternatively, a fluorescent substance is coated in advance onto an endoscopic examination subject and the fluorescent light emitted from the fluorescent substance when, in the same way, the light of the specific wavelength is irradiated thereon is observed. Moreover, in the endoscope device described in Japanese Patent No. 3194660, a diffusion optical component such as a diffusion lens is attached to the outgoing end of the laser light on the distal end side of the insertion portion, so that the laser light of the specific wavelength is diffused and then irradiated onto the endoscopic examination subject.

When an endoscopic observation that uses this technology is performed in parallel with a normal endoscopic observation, a light source that emits white light and a laser light source that emits light of a specific wavelength are provided in advance, and the observation light is switched by appropriately selecting one of these light sources.

SUMMARY OF THE INVENTION

In order to achieve the above described object this invention provides an endoscope device that includes: a laser light source that emits light having a specific wavelength; a diffusion optical component that diffuses light emitted from the laser light source and irradiates it onto an endoscopic examination subject at a distal end portion of an insertion portion; an adaptor that has a fluorescent substance that uses light from the laser light source as excitation light to emit light having a different wavelength, and is mounted on the distal end portion of the insertion portion such that it is able to be freely attached or removed; and a diffusion prevention component that is placed between the fluorescent substance of the adaptor and the diffusion optical component, and that prevents diffusion of light irradiated from the diffusion optical component.

DESCRIPTION OF THE PREFERRED EMBODIMENTS

The respective embodiments of this invention will be described based on the drawings. Note that the same symbols are used for the same portions in each embodiment and a description of any duplicated portions is omitted.

Firstly, the first embodiment shown in FIGS. 1 through 4 will be described.

Figure 1:
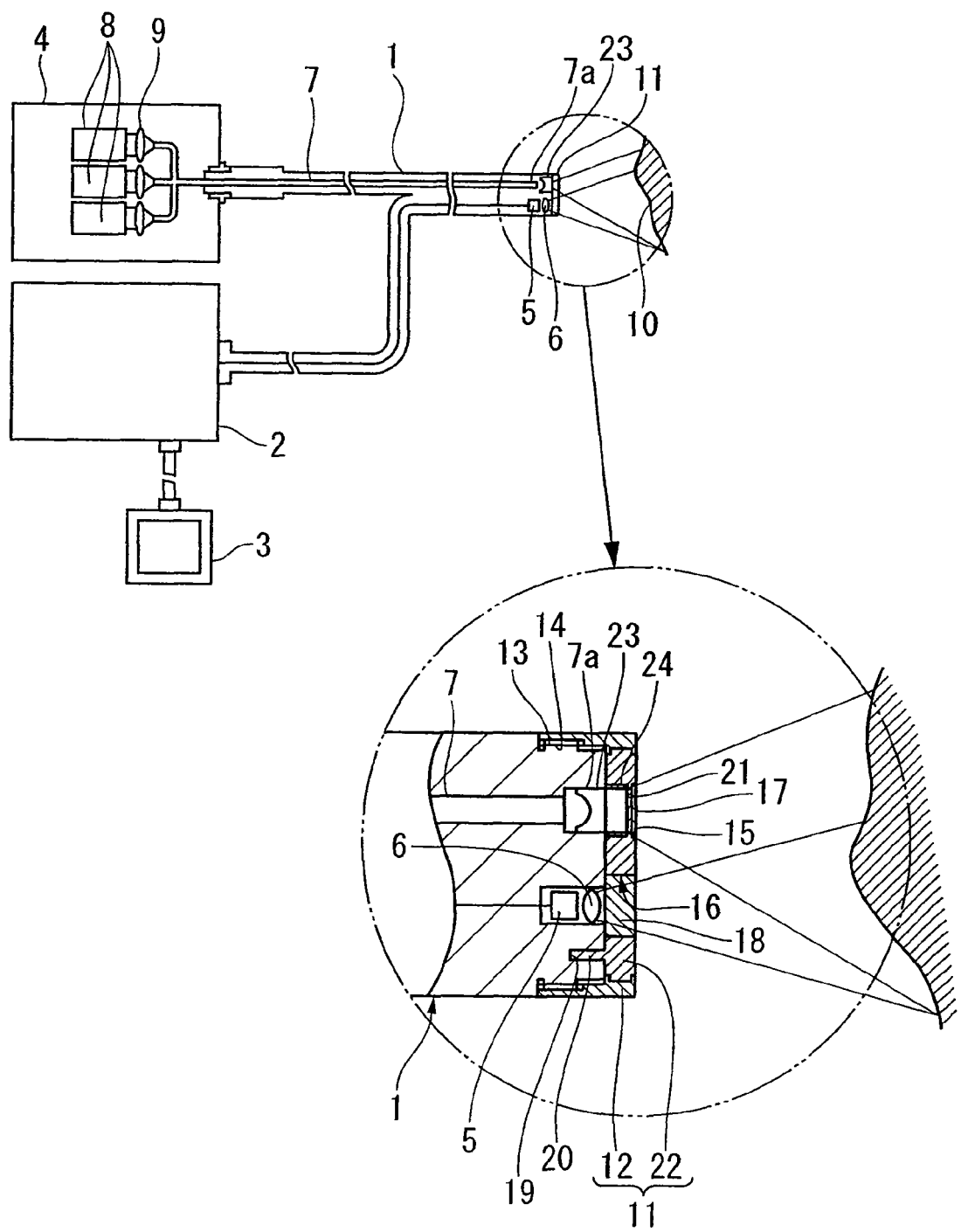
FIG. 1 shows a first embodiment of the endoscope device of the present invention and is a schematic structural view of when an adaptor is fitted to this endoscope device.

FIG. 1 shows the overall structure of the endoscope device according to this invention. This endoscope device is provided with an insertion portion 1 that is inserted into a lumen or the like of an endoscopic examination subject, an image processing unit 2 that processes image signals and displays them on a display unit 3, and a light source unit 4 that produces illumination light.

In the insertion portion 1 are provided an image pickup device in the form of a charge coupled device 5 (referred to below as a CCD 5), an observation optical component 6 such as an objective lens that links together images of an endoscopic examination object 10 on the CCD 5, and a light guide 7 that is formed by an optical fiber or the like. The light guide 7 guides light produced by the light source unit 4 to a distal end of the insertion portion 1. In addition, a diffusion optical component 23 such as a diffusion lens that diffuses light from a laser light source and irradiates it in a forward direction is provided at a position facing an outgoing end 7a of the light guide 7 at the distal end of the insertion portion 1. Moreover, the image processing unit 2 inputs image signals captured by the CCD 5 into a signal processing circuit (not shown), and projects signals processed by the signal processing circuit on the display unit 3 as video images. The light source unit 4 is provided with a laser light source in the form of a plurality of laser diodes 8 that emit light of a specific wavelength, and a condensing optical component 9 that condenses light generated by the respective laser diodes 8 in the light guide 7. The laser diodes 8 used here generate light having a wavelength of 450 nm or less.

Note that the image processing unit 2, the display unit 3, and the light source unit 4 may be formed as a single block on the base portion side of the insertion portion 1, or each of these may be formed as an independent block with the respective blocks connected together by a cable.

Figure 2:
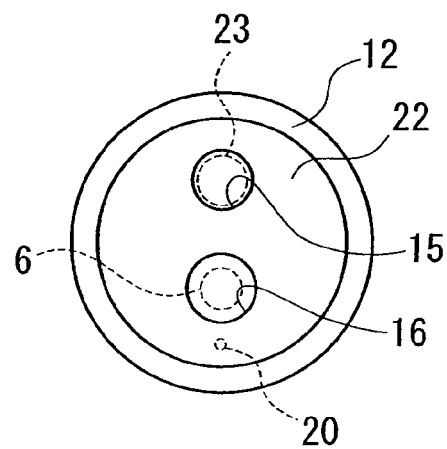
FIG. 2 shows the aforementioned first embodiment and is a frontal view of principal portions when an adaptor is fitted.
Figure 3:
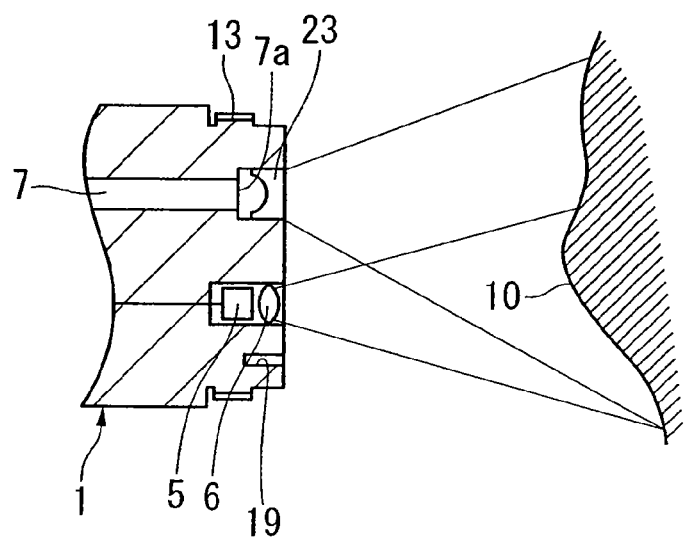
FIG. 3 shows the aforementioned first embodiment and is a cross-sectional view of principal portions when an adaptor is not fitted.
Figure 4:
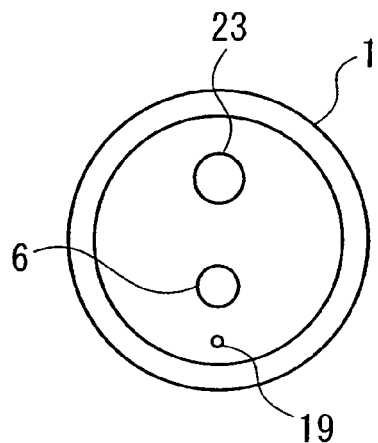
FIG. 4 shows the aforementioned first embodiment and is a frontal view of principal portions when an adaptor is not fitted.

A male screw 13 (i.e., screw fitting portion) is formed on an outer circumference of the distal end portion of the insertion portion 1, and an adaptor 11 can be fitted onto this male screw 13 portion. FIGS. 1 and 2 show a state in which the adaptor 11 is mounted on the distal end of the insertion portion 11. FIGS. 3 and 4 show a state in which the adaptor 11 has been removed. As is shown in FIG. 1, the adaptor 11 holds a fluorescent substance 21 that, using light from the laser diode 8 as excitation light, emits light of a different wavelength. The adaptor 11 is mounted on the insertion portion 1 so as to adhere to a front surface of the distal end of the insertion portion 1. Specifically, the adaptor 11 is provided with a substantially cylindrical holder 12 and a cylindrical plate-shaped front surface plate 22 that is held on the front end portion of this holder 12 such that it can rotate freely. A female screw 14 (i.e., screw fitting portion) that is screwed together with the male screw 13 of the insertion portion 1 is formed on an inner circumferential surface on a rear portion side of the holder 12. This male screw 13 and female screw 14 constitute an adaptor anchoring portion.

On the front surface plate 22 there are provided an illumination window 15 for the diffusion optical component 23 on the distal end of the insertion portion 1, and an observation window 16 for the observation optical component 6 that is also on the distal end of the insertion portion 1. A protective glass 17 that covers the fluorescent substance 21 that is formed in a circular plate shape and also covers the front surface of this fluorescent substance 21 is mounted on the illumination window 15. Only a protective glass 18 is provided on the observation window 16. A cylindrical reflective component 24 whose inner circumferential surface is a mirror surface is mounted in the illumination window 15 on a rear portion side of the fluorescent substance 21. This cylindrical reflective component 24 constitutes a diffusion prevention component of the present invention and the diameter of the reflective surface of the inner circumference thereof is set so as to be the same as or slighter larger than the outer diameter of the diffusion optical component 23.

Moreover, a positioning recessed portion 19 is formed at a position that is offset from the center of the front end surface of the insertion portion 1, and an anchoring projection 20 that fits into this positioning recessed portion is formed in a rear surface of the front surface plate 22. The positioning structure that is made up by this anchoring projection 20 and positioning recessed portion 19 is provided so that the illumination window 15 is always placed correctly at the front surface of the diffusion optical component 23 and so that the observation window 16 is always placed correctly at the front surface of the observation optical component 6. Namely, the adaptor 11 is screwed onto the insertion portion 1 by engaging the anchoring projection 20 with the positioning recessed portion 19 so as to position the front plate 22 on the insertion portion 1, and by then rotating only the holder 12 in this state.

Here, the fluorescent substance 21 that is used is one that receives excitation light in the form of laser light and emits light that includes light having a wavelength of 400 nm to 650 nm, and irradiates white light in a forward direction.

As has been described above, in the endoscope device of this embodiment, because the adaptor 11 that is provided with the fluorescent substance 21 is removably attached to the distal end portion of the insertion portion 1, it is possible to switch easily between the irradiation of light having a specific wavelength of 450 nm or less and the irradiation of white light simply by attaching or removing the adaptor 11.

Namely, as is shown in FIGS. 3 and 4, when the adaptor 11 is removed from the insertion portion 1, the light of a specific wavelength that has been emitted from the laser diode 8 is diffused by the diffusion optical component 23 at the outgoing end 7a of the light guide 7, and is irradiated onto the endoscopic examination subject 10 as diffused light. Moreover, as is shown in FIGS. 1 and 2, when the adaptor 11 is attached to the insertion portion 1, the light of a specific wavelength that has entered into the diffusion optical component 23 from the outgoing end 7a of the light guide 7 and has been temporarily diffused is condensed by the cylindrical reflective component 24 of the adaptor 11 and almost the entire amount of the condensed light passes through the fluorescent substance 21. At this time, the light of a specific wavelength becomes the excitation light for the fluorescent substance 21 and is changed into white light and irradiated onto the endoscopic examination subject 10.

Accordingly, in this endoscope device, because it is possible to switch between an observation made using light of a specific wavelength and an observation made using white light using the laser diode 8 as a shared light source, it is possible to avoid any increase in the size of the device that is due to an increase in the number of light sources. Moreover, in this device, because it is possible when the adaptor 11 is fitted to irradiate light of a specific wavelength that has been diffused by the diffusion optical component 23 reliably and efficiently onto the fluorescent substance 21 using the cylindrical reflective component 24, sufficient white light can be irradiated onto the endoscopic examination subject 10 without generating any increase in the placement surface area of the fluorescent substance 21. In addition, because the placement surface area of the fluorescent substance 21 can be decreased, the diameter of the distal end of the insertion portion 1 including the adaptor 11 can be reduced.

Moreover, the device of this embodiment has the advantage that because the laser diode 8 is used as a light source, the size of the light source unit 4 of the device can be reduced.

Moreover, in this endoscope device, a plurality of types of adaptor 11 in which the characteristics of the fluorescent substances 21 are different are prepared in advance, and thereby a variety of observations can be dealt with flexibly.

Furthermore, in this embodiment, the adaptor 11 was made so that it could be freely attached or removed by screwing or unscrewing the male screw 13 and the female screw 14, however, it is also possible to make the adaptor 11 so that it can be attached or removed freely using a locking screw or a locking structure that interlocks a catch and a recess. However, a screw structure is employed as in the present embodiment, and thereby not only can the tightness of the adaptor 11 be adjusted, but the attachment or removal operation is also simplified.

Moreover, in the device of this embodiment, the cylindrical reflective component 24 that condenses the light of a specific wavelength that has passed through the diffusion optical component 23 is formed integrally with the adaptor 11, however, it is also possible for the cylindrical reflective component 24 to be formed independently from the adaptor 11 and for it to be interposed between the diffusion optical component 23 and the fluorescent substance 21 when the adaptor 11 is being fitted. However, the cylindrical reflective component 24 is formed integrally with the adaptor 11 so as to be superposed on the rear surface of the fluorescent substance 21, as in the present embodiment, and thereby this has the advantage that the cylindrical reflective component 24 can be easily and accurately placed between the diffusion optical component 23 and the fluorescent substance 21 simply by fitting the adaptor 11 onto the distal end of the insertion portion 1. In particular, the front surface plate 22 has been accurately positioned on the insertion portion 1 using the anchoring projection 20 and the positioning recessed portion 19, as in this embodiment, and thereby it is possible to reliably prevent any leakage of diffused light that is due to mispositioning of the diffusion optical component 23 and the cylindrical reflective component 24.

It should be noted that, in the above description, a structure is employed in which white light is obtained by employing the fluorescent substance 21 that receives excitation light in the form of laser light and emits light including light having a wavelength of 400 nm to 650 nm, however, it is also possible to provide a structure in which a fluorescent substance 21 that receives excitation light and emits light having a wavelength of 600 nm or greater is employed, so that infrared light is irradiated onto the observation subject 10. Moreover, depending on the observation target, it is also possible to use a fluorescent substance 21 that receives excitation light and emits light having a different wavelength from the excitation light that has a wavelength of 450 nm or less.

Figure 5:
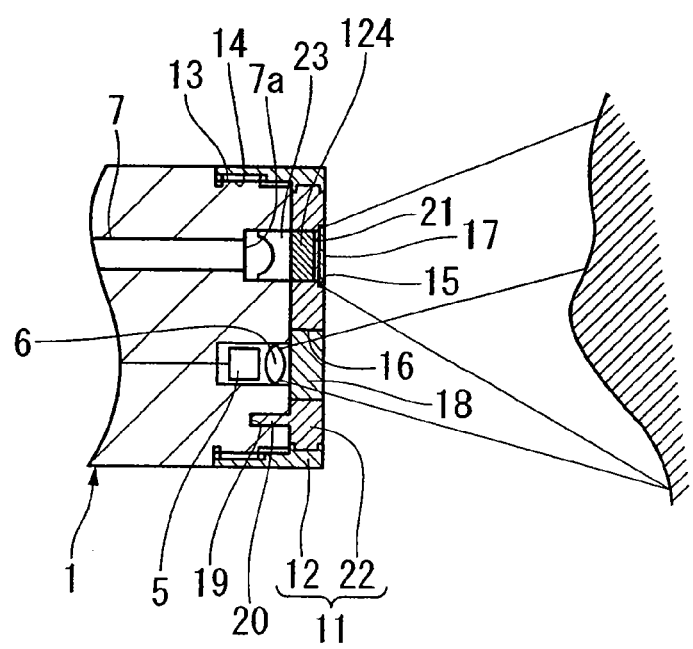
FIG. 5 shows a second embodiment of the endoscope device of the present invention and is a cross-sectional view of principal portions when an adaptor is fitted to this endoscope device.

Next, a description will be given of the second embodiment shown in FIG. 5.

The endoscope device 1 shown in this embodiment has substantially the same basic structure as that of the first embodiment, however, the diffusion prevention component that is mounted on the illumination window 15 of the adaptor 11 is considerably different from the diffusion prevention component of the first embodiment. Namely, the diffusion prevention component of this embodiment is formed from glass or resin or the like, and the inner circumferential surface thereof is a circular column-shaped transparent solid component 124 that reflects light.

In this case as well, in the same way as in the first embodiment, light that has been diffused by the diffusion optical component 23 is reflected by the inner circumferential surface of the transparent solid component 124, and this light can be reliably irradiated onto the fluorescent substance 21.

Note that the transparent solid component 124 may be formed entirely from a uniform substance having the same index of refraction, however, it may also be formed as a structure having a core and cladding that are formed by components that each have a different index of refraction. In this case, the inner surface of the outer circumference of the core becomes the light reflective surface.

In the same way as in the first embodiment, in the device of this embodiment, using a laser light source that emits light of a specific wavelength as a shared light source, it is possible to make observations using light having a plurality of wavelengths simply by attaching or removing the adaptor 11. Moreover, when fitting the adaptor 11, light that has been diffused by the diffusion optical component 23 can be irradiated efficiently onto the fluorescent substance 21 by the transparent solid component 124.

Figure 6:
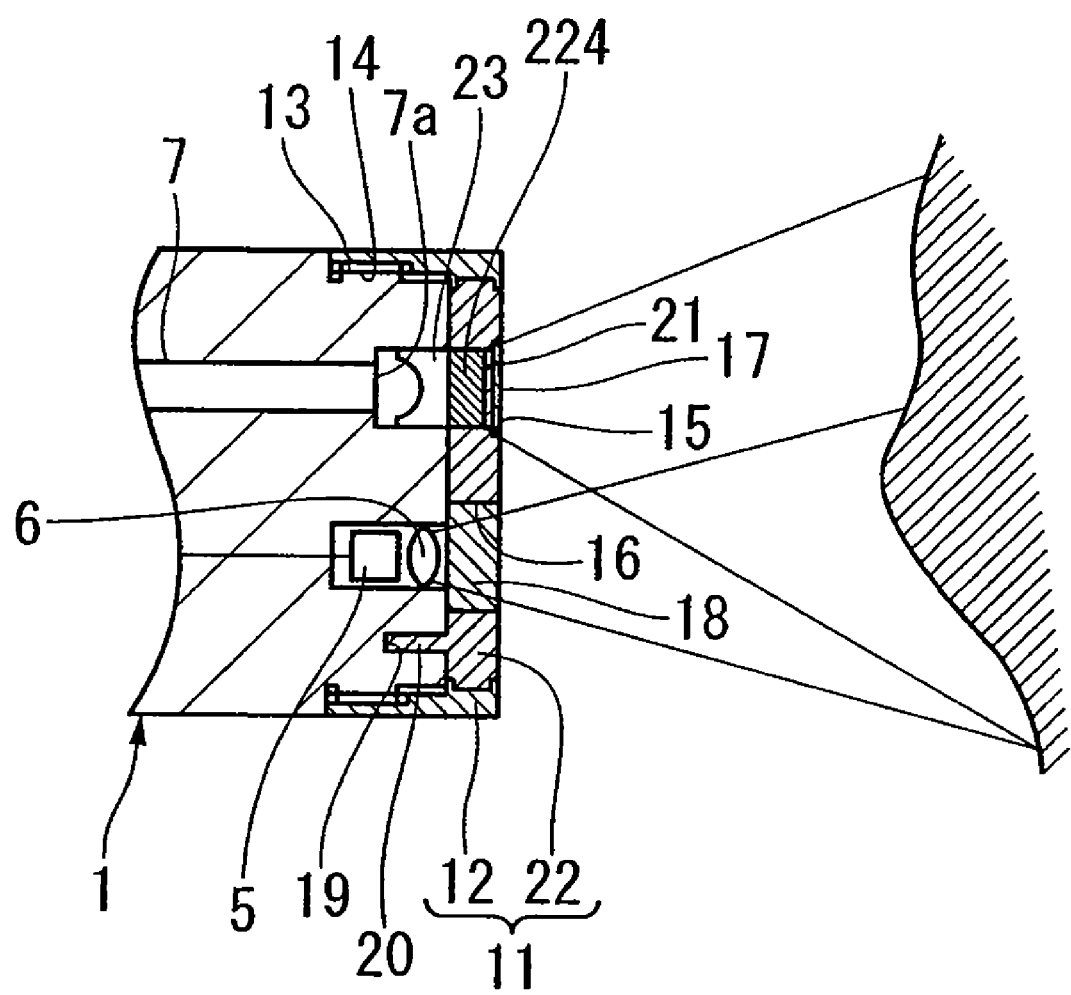
FIG. 6 shows another embodiment of the endoscope device of the present invention and is a cross-sectional view of principal portions when an adaptor is fitted.

While preferred embodiments of the invention have been described and illustrated above, it should be understood that these are exemplary of the invention and are not to be considered as limiting. Additions, omissions, substitutions, and other modifications can be made without departing from the spirit or scope of the present invention. Accordingly, the invention is not to be considered as limited by the foregoing description and is only limited by the scope of the appended claims. For example, the diffusion prevention component that is mounted on the adaptor 11 may also be a condensing optical component 224 that is formed by a single lens or a plurality of lenses, as is shown in FIG. 6.

The present invention relates to an endoscope device that includes: a laser light source that emits light having a specific wavelength; a diffusion optical component that diffuses light emitted from the laser light source and irradiates it onto an endoscopic examination subject at a distal end portion of an insertion portion; an adaptor that has a fluorescent substance that uses light from the laser light source as excitation light to emit light having a different wavelength, and is mounted on the distal end portion of the insertion portion such that it is able to be freely attached or removed; and a diffusion prevention component that is placed between the fluorescent substance of the adaptor and the diffusion optical component, and that prevents diffusion of light irradiated from the diffusion optical component. According to the endoscope device of the present invention, because it is possible to switch between a diffusion irradiation onto an endoscopic examination subject that uses light having a specific wavelength and an irradiation of light having a different wavelength from this simply by attaching or removing an adaptor, it is possible to achieve a switch in observation light without generating any increase in the number of light sources or increase in the size of the device.

What is claimed is:

1. An endoscope device comprising:
   a laser light source that emits light having a specific wavelength;
   a light guide that guides light produced by the laser light source;
   a diffusion lens that diffuses light emitted from the light guide and irradiates the diffused light onto an endoscopic examination subject at an end portion of an insertion portion;
   an adaptor that has a fluorescent substance that uses light from the light guide as excitation light and emits light having a different wavelength, and is configured to be removably mounted on the end portion of the insertion portion; and
   a diffusion prevention component between the fluorescent substance of the adaptor and the diffusion lens, configured to prevent diffusion of light irradiated from the diffusion lens.

2. The endoscope device according to claim 1, wherein the diffusion prevention component is mounted integrally on the adaptor.

3. The endoscope device according to claim 1, wherein the adaptor is able to be mounted on or removed from the insertion portion using a screw fitting portion that is provided between the distal end portion of the insertion portion and the adaptor.

4. The endoscope device according to claim 1, wherein the diffusion prevention component is a cylindrical component and a mirror surface is provided on an inner circumference of the diffusion prevention component, and light from the laser light source passes through an inner side of the diffusion prevention component.

5. The endoscope device according to claim 1, wherein the diffusion prevention component is a transparent solid component whose inner circumferential surface reflects light.

6. The endoscope device according to claim 1, wherein the diffusion prevention component is a transparent solid component having a core and cladding, and an inner surface of an outer circumference of the core reflects light.

7. The endoscope device according to claim 1, wherein the diffusion prevention component is a condensing lens.

8. The endoscope device according to claim 1, wherein the light emitted by the laser light source is light having a wavelength of 450 nm or less.

9. The endoscope device according to claim 1, wherein the laser light source is a laser diode.

10. The endoscope device according to claim 1, wherein the fluorescent substance receives the excitation light and emits light that includes a wavelength of 400 nm to 650 nm.

11. The endoscope device according to claim 1, wherein the adaptor changes light irradiated from the diffusion lens into white light, as a result of being fitted onto the distal end of the insertion portion.

12. The endoscope device according to claim 1, wherein the fluorescent substance receives excitation light and emits light having a wavelength of 600 nm or more.

13. The endoscope device according to claim 1, wherein the fluorescent substance receives excitation light and emits light having a different wavelength from the excitation light that is 450 nm or less.

* * * * *